United States Patent [19]

Sugimori et al.

[11] Patent Number: 5,100,795

[45] Date of Patent: Mar. 31, 1992

[54] BILE ACID SULFATE SULFATASE, PROCESS FOR ITS PREPARATION AND METHOD FOR ASSAYING BILE ACID

[75] Inventors: Tsunetake Sugimori, Uji; Yoji Tsukada, Kyoto; Yasuhiko Tatsuke, Ashiya, all of Japan

[73] Assignee: Marukin Shoyu Co., Ltd., Kagawa, Japan

[21] Appl. No.: 684,799

[22] Filed: Apr. 15, 1991

Related U.S. Application Data

[62] Division of Ser. No. 548,932, Jul. 26, 1990.

[30] Foreign Application Priority Data

Nov. 28, 1988 [JP] Japan .................................. 63-301415

[51] Int. Cl.⁵ .............................................. C12N 9/16
[52] U.S. Cl. ................................... 435/196; 435/233; 435/19
[58] Field of Search ........................ 435/196, 233, 19

[56] References Cited

U.S. PATENT DOCUMENTS 4,889,801 12/1989 Ushizawa .............................. 435/25

OTHER PUBLICATIONS

Takagi et al., Vitamins (Japan) 60:165-172 (1986).
Imperato et al., Clin. Res. 25:109A (1977).
Huijghebaert et al., App. and Env. Micro. 44:1030-34 (1982).

*Primary Examiner*—Douglas W. Robinson
*Assistant Examiner*—Sandra Sancier
*Attorney, Agent, or Firm*—Larson and Taylor

[57] ABSTRACT

The invention provides a novel bile acid sulfate sulfatase, a process for its preparation, and a method of assaying bile acid 3α-sulfates and total bile acids using the bile acid sulfatase.

1 Claim, 6 Drawing Sheets

○ ··· Tris buffer solution
△ ··· Pyrophosphate buffer solution
× ··· Phosphate buffer solution

BILE ACID SULFATE SULFATASE, PROCESS FOR ITS PREPARATION AND METHOD FOR ASSAYING BILE ACID

This is a division of application Ser. No. 07/548,932, filed July 26, 1990.

FIELD OF THE INVENTION

The present invention relates to bile acid sulfate sulfatase, its preparation and methods of quantitatively determining bile acid.

The enzyme of the invention is a useful novel enzyme for clinical examinations, and is useful for the determination of sulfated bile acids such as bile acids in which the OH group at 3-position is sulfated (hereinafter referred to as bile acid 3α-sulfate), and for the determination of bile acid in blood or urine.

PRIOR ART

It is well known that the bile acid in blood or urine markedly increases due to hepatobiliary diseases. It is therefore an important item to determine the bile acid in blood or urine for evaluating the hepatic function in clinical examinations. Conventional method of determining bile acid adopts the enzymatic analysis method wherein 3α-hydroxysteroid dehydrogenase is employed. Said dehydrogenase oxidizes bile acids wherein the 3-position OH group is in α-configuration (3α-hydroxy bile acid) to 3-oxo bile acids, and concurrently reduces the coenzyme β-NAD to NADH. By determining the NADH, the 3α-hydroxy bile acids are determined. In the conventional clinical examination, the quantity of 3α-hydroxy bile acids is regarded as the total amount of bile acids.

However, bile acids in blood are present in part as sulfated bile acids which have been sulfated, and the hydrophilic property is enhanced by the sulfation and the excretion thereof is facilitated, so that the ratio of sulfated bile acids, in particular bile acid 3α-sulfates, in urine is extremely increased. The dehydrogenase in the prior art method acts only on the 3α-hydroxy bile acids, and hence in the prior art method it is impossible to determine the bile acid 3α-sulfates wherein the 3α-hydroxyl group has been sulfated. In clinical examinations, it is necessary to determine the total bile acid 3α-sulfates or the total bile acids including it in urine or blood, but bile acid sulfatase capable of specifically hydrolyzing the sulfate ester moiety of the bile acid 3α-sulfates is not known yet.

Under the circumstances, in order to determine the bile acid 3α-sulfates, a sample therefor must be subjected to a column chromatography to separate bile acid 3α-sulfates, and then the sulfate moiety of the bile acid 3α-sulfates must be chemically hydrolyzed by solvolysis. Such process is, however, very cumbersome and cannot be used easily in the daily clinical examinations.

DISCLOSURE OF THE INVENTION

It is an object of the invention to provide a novel bile acid sulfate sulfatase capable of specifically hydrolyzing the sulfate ester moiety of bile acid 3α-sulfates.

It is another object of the invention to provide a method for the preparation of such bile acid sulfate sulfatase.

It is another object of the invention to provide a method capable of easily determining the total bile acid 3α-sulfates in blood or urine which were impossible to measure in the conventional enzymatic method.

It is a further object of the invention to provide a method capable of easily determining the total bile acids, including the bile acid 3α-sulfates, in blood or urine.

Other objects and features of the invention will become apparent from the following description.

The present invention provides a bile acid sulfate sulfatase, its preparation, and methods of determining bile acids, as defined in 1 to 4 below.

1. A bile acid sulfate sulfatase having the following properties:

(a) Action: Acting on 3α-sulfates of bile acids to hydrolyze the sulfate ester moiety thereof and to invert the bonding configuration of the resulting OH group from α-configuration to β-configuration, thereby producing 3β-hydroxy bile acids;

(b) Substrate specificity: Acting on 3α-sulfates of nonconjugate bile acids, and 3α-sulfates each of glycine-conjugated and taurine-conjugated bile acids; and (c) Optimum pH range: pH 8.5±0.5.

2. A method for the preparation of a bile acid sulfate sulfatase comprising culturing *Pseudomonas testosteroni* in a culture medium containing bile acid, and recovering the bile acid sulfate sulfatase of claim 1 from the resulting culture.

3. A method of determining 3α-sulfates of bile acids comprising causing a bile acid sulfate sulfatase and β-hydroxysteroid dehydrogenase to act on a sample containing 3α-sulfates of bile acids in the presence of β-NAD, and determining the produced NADH.

4. A method of determining total bile acid comprising causing a bile acid sulfate sulfatase, β-hydroxysteroid dehydrogenase and 3α-hydroxysteroid dehydrogenase to act on a sample containing 3α-sulfates of bile acids and other bile acid(s) in the presence of β-NAD, and determining the produced NADH.

The present inventors, as a result of intensive researches, succeeded in obtaining a novel bile acid sulfate sulfatase capable of specifically hydrolyzing the sulfate ester moiety of bile acid 3α-sulfates, and discovered that total bile acid 3α-sulfates in blood or urine which could not be measured by the conventional enzymatic method can be easily determined by coupling said enzyme and β-hydroxysteroid dehydrogenase in the presence of β-NAD, and also found that total bile acids including the bile acid 3α-sulfates in blood or urine could be easily determined by coupling said enzyme, β-hydroxysteroid dehydrogenase and 3α-hydroxysteroid dehydrogenase in the presence of β-NAD, and thereby completed the invention.

The bile acid sulfate sulfatase of the invention (hereinafter referred to as the present Enzyme) is an enzyme produced by *Pseudomonas testosteroni*.

The physicochemical properties of the present Enzyme are further described below. The activity of the present Enzyme is measured as follows. That is, into a quartz cell are placed 0.1 ml of 2.5 mM aqueous solution of lithocholic acid 3α-sulfate (Sigma), 0.2 ml of 15 mM aqueous solution of β-NAD (Oriental Yeast), 1.0 ml of 0.1 M tris-hydrochloric acid buffer solution (pH 8.0) and 1.55 ml of distilled water, and after equilibrating at 30° C., 0.05 ml of β-hydroxysteroid dehydrogenase (Sigma) solution (10 U/ml) and 0.1 ml of a solution of the present Enzyme are sequentially added thereto and the reaction is effected at 30° C., and the increase of the absorbance at 340 nm in the initial stage of the reaction is determined. Under these conditions, the enzyme activity producing 1 μmol of NADH per minute is defined as 1 unit.

(a) Action: Acting on 3α-sulfates of bile acids to hydrolyze the sulfate ester moiety and to invert the bonding configuration of the resulting OH group from α-configuration to β-configuration, thereby producing 3β-hydroxy bile acids.

(b) Substrate specificity: Acting on 3α-sulfates of nonconjugated bile acids, and 3α-sulfates each of glycine-conjugated and taurine-conjugated bile acids. The details are shown in Table 1.

TABLE 1

| Substrate | Relative activity (%) |
| --- | --- |
| Lithocholic acid 3α-sulfate | 100 |
| Glycolithocholic acid 3α-sulfate | 11 |
| Taurolithocholic acid 3α-sulfate | 2 |
| Cholic acid 3α-sulfate | 238 |
| 3β-Hydroxy-5-cholenic acid 3-sulfate | 0 |
| 4-Nitrocatechol sulfate | 0 |
| p-Nitrophenyl sulfate | 0 |

(c) Optimum pH: pH 8.5±0.5 (FIG. 1). FIG. 1 is a graph showing the relation of the realtive activity of the present Enzyme and pH.

(d) pH stability: pH 5.6–7.6 (FIG. 2). FIG. 2 is a graph showing the relation of the realtive activity of the present Enzyme and pH when the present Enzyme is left to stand at 30° C. for 16 hours.

(e) Optimum temperature: 35° C. ±5° C. (FIG. 3). FIG. 3 is a graph showing the relation between the realtive activity of the present Enzyme and temperature.

(f) Thermal stability: When the present Enzyme is left to stand at pH 7.2 for 10 minutes, the activity remains by 100% at a temperature of 32° C. or lower, but at higher temperatures the activity rapidly decreases and becomes 0% at 50° C. (FIG. 4). FIG. 4 is a graph showing the thermal stability of the present Enzyme.

(g) Molecular weight: As a result of measurement by high performance liquid chromatography using gel filtration column Shim-pack Diol-300 (Shimadzu), the molecular weight is calculated to be about 100,000.

(h) Km value: The Km value to lithocholic acid 3α-sulfate: $6 \times 10^{-6}$M.

(i) Inhibition and activation: Activated by $Mn^{++}$ and inhibited by the substances acting on metal ions, such as EDTA and o-phenanthroline, etc. Hardly inhibited by SH reagents such as p-chloromercuribenzoate and monoiodoacetic acid. Details are shown in Table 2.

TABLE 2

| Additives | Concentration (mM) | Relative Activity (%) |
| --- | --- | --- |
| No additive (control) | — | 100 |
| Magnesium sulfate | 2 | 101 |
| Manganese chloride | 2 | 111 |
| Cobalt chloride | 2 | 92 |
| Copper sulfate | 2 | 94 |
| Zinc sulfate | 2 | 95 |
| Cadmium chloride | 2 | 98 |
| Mercuric chloride | 1 | 90 |
| Mercuric chloride | 2 | 71 |
| EDTA | 1 | 38 |
| EDTA | 5 | 25 |
| o-Phenanthroline | 1 | 37 |
| α,α'-Dipyridyl | 1 | 97 |
| p-Chloromercuribenzoate | 0.2 | 98 |
| Monoiodoacetic acid | 2 | 98 |
| Sodium fluoride | 2 | 98 |
| Sodium azide | 10 | 100 |

The present Enzyme is collected from the culture of Pseudomonas testosteroni. The Pseudomonas testosteroni (hereinafter called this organism) is not particularly limited, and any known strain may be used. Above all, Pseudomonas testosteroni ATCC11996 or the like is preferable.

The culture medium for use in the cultivation of this organism is not particularly limited, and any culture medium may be used as far as the bacteria of the genus Pseudomonas can grow therein, and examples thereof include those containing yeast extract, peptone, meat extract or the like as the organic nutrient sources, ammonium phosphate, ammonium nitrate, potassium phosphate, sodium phosphate, magnesium chloride and manganese chloride as the inorganic nutrient sources. Furthermore, to produce the present Enzyme, it is essential to add a bile acid to the culture medium. Usable bile acids include, for example, cholic acid, deoxycholic acid, chenodeoxycholic acid, lithocholic acid sulfate and their salts, and these can be used singly or at least two of them may be used in combination. The amount of bile acid to be used is not particularly limited, but is usually about 0.01 to 2.0 wt.%, preferably about 0.05 to 1.0 wt.%.

The cultivation is preferably done in aerobic condition. The cultivation time and temperature are not particularly limited, but the cultivation temperature is usually about 22° to 35° C., preferably about 26° to 30° C., and the cultivation time is usually about 8 to 30 hours, preferably about 12 to 24 hours. By cultivation for about 12 to 24 hours, the enzyme activity reaches its maximum.

From the bacterial cells harvested by the cultivation, the present Enzyme can be obtained by, for example, extraction. The extraction is done according to the conventional extraction methods of enzymes in bacterial cells. For example, the bacterial cells are destroyed by ultrasonication, various mechanical processing or enzyme treatment, and then centrifuged to separate the insoluble matter, whereby a supernatant containing the present Enzyme (crude enzyme solution) is obtained. By purifying this crude enzyme solution by properly selecting and combining commonly employed enzyme purification methods such as the treatment to remove nucleic acids, ammonium sulfate salting-out, ion exchange chromatography, hydrophobic chromatography and gel filtration, the present Enzyme can be isolated.

The present Enzyme thus obtained and β-hydroxysteroid dehydrogenase are caused to act on a sample containing bile acid 3α-sulfates in the presence of β-NAD, and thereby the bile acid 3α-sulfates are determined. That is, the present Enzyme converts the bile acid 3α-sulfates into 3β-hydroxy bile acids, and then the β-hydroxysteroid dehydrogenase converts the 3β-hydroxy bile acids into 3-oxobile acids and concurrently reduces the NAD which is the coenzyme of said dehydrogenase into NADH. Therefore, when the conversion quantity from NAD into NADH is determined, the bile acid 3α-sulfates are determined.

The β-hydroxysteroid dehydrogenase is not particularly limited, and any known ones may be used.

The amounts of the enzymes to be used are not particularly limited, but usually the present Enzyme is used in an amount of about 0.04 to 2.0 units, preferably 0.1 to 1.0 unit, and the β-hydroxysteroid dehydrogenase is usually used in an amount of about 0.05 to 2.0 units, preferably 0.1 to 1.0 unit. The amount of β-NAD to be used is also not particularly limited, but it may be added such that the β-NAD concentration in the reaction system is usually about 0.1 to 10 mM, preferably about 0.5 to 5 mM. The enzyme reaction is usually conducted at a temperature of about 20° to 40° C., preferably about 25° to 37° C., and for about 5 to 60 minutes, preferably about 10 to 30 minutes.

The NADH may be determined by a known method such as UV (340 nm) absorption measurement, fluorescence intensity measurement, reductive coloring colorimetry, or calorimetric method wherein NADH oxidase is caused to act on NADH to quantitatively generate from the NADH hydrogen peroxide which in turn is calorimetrically determined by oxidative coloration.

Furthermore, in this invention, total bile acids including bile acid 3α-sulfate can be determined by causing 3α-hydroxysteroid dehydrogenase, in addition to the present Enzyme and β-hydroxysteroid dehydrogenase, to act in the presence of β-NAD on a sample containing bile acid 3α-sulfates and other bile acid(s). When urine or blood is used as the sample containing bile acid 3α-sulfates and other bile acid(s), the total bile acids in blood or urine are determined.

The 3α-hydroxysteroid dehydrogenase is not particularly limited, and any known ones may be used. The amount of the dehydrogenase to be used is not particularly limited, but it is usually about 0.04 to 2.0 units, preferably about 0.1 to 1.0 unit. The amounts of other enzymes (the present Enzyme and β-hydroxysteroid dehydrogenase) and β-NAD, reaction conditions, and method of determination of the produced NADH may be the same as in the case of determination of bile acid 3α-sulfates.

EXAMPLE

Examples are given below, but it must be noted that the invention is not limited to these examples. In the examples, "%" means "wt.%".

EXAMPLE 1

A 300 ml quantity of a culture medium (pH 6.9) comprising 0.1% ammonium dihydrogen phosphate, 0.1% diammonium hydrogen phosphate, 0.2% potassium dihydrogen phosphate, 0.01% magnesium chloride, 0.01% manganese chloride and 1.0% yeast extract was placed in a 2-liter Erlenmeyer flask, and was sterilized in an autoclave. *Pseudomonas testosteroni* ATCC11996 was inoculated, and was cultivated for 24 hours at 28° C. under shaking. This seed culture broth was inoculated on 30 liters of sterilized culture medium of the same composition as above in a 50-liter jar fermenter, and at the same time 1.2 liters of 10% sodium cholate aqueous solution separately sterilized was aseptically added thereto, and the cultivation was continued for 15 hours at 28° C. under aeration and stirring.

The culture broth was centrifuged, and the obtained bacterial cells were suspended in 30 mM phosphate buffer solution (pH 7.2), and this suspension was applied to a DYNO-Laboratory mill (Willy A. Bachofen Mashinefabrik) to disrupt the cells. By centrifugation, the resulting sediments were removed, and crude enzyme solution was obtained. The crude enzyme solution was treated with protamine sulfate to remove nucleic acid, followed by salting-out with use of ammonium sulfate. The fraction precipitated under ammonium sulfate fractionation of 35 to 70 % saturation was collected, and dialyzed against 10 mM phosphate buffer solution (pH 7.2). The dialysate was passed through a column of DEAE cellulose (Whatman) equilibrated with 10 mM phosphate buffer solution (pH 7.2). The obtained non-adsorbed fractions were passed through a column of DEAE Sepharose CL-6B (Pharmacia) equilibrated with 5 mM tris-hydrochloric acid buffer solution (pH 8.0). The obtained non-adsorbed fractions were concentrated by salting-out treatment with use of ammonium sulfate, and allowed to be adsorbed on octyl Sepharose CL-4B (Pharmacia) column. Through this column 50 mM phosphate buffer solution was passed, and the eluting active fractions were concentrated by ultrafiltration, followed by gel filtration by passing through a column of Sephacryl S-200 (Pharmacia) equilibrated with 50 mM phosphate buffer solution containing 0.15 M sodium chloride. The active fractions were desalted and concentrated by ultrafiltration, thereby giving 480 units of bile acid sulfate sulfatase. The purified product gave a single band in slab gel electrophoresis with use of 7.5% acrylamide (pH 8.9).

EXAMPLE 2

Using the bile acid sulfate sulfatase obtained in Example 1, bile acid 3α-sulfate was determined.

Each of aqueous solutions (0.1 ml each) of lithocholic acid 3α-sulfate, sodium salt (Sigma) or glycolithocholic acid 3α-sulfate, sodium salt (Sigma) having different concentrations was added, as substrate, to 2.9 ml of 35 mM tris-hydrochloric acid buffer solution (pH 8.0) containing 3 μmol of β-NAD (Oriental Yeast), 0.5 unit of β-hydroxysteroid dehydrogenase (Sigma) and 0.2 unit of bile acid sulfate sulfatase, and the mixture was allowed to react for 10 minutes at 30° C., and then the absorbance at 340 nm was measured. The results are shown in FIG. 5, from which it is seen that the concentration of the substrate and the absorbance are in positive correlation, thereby showing that the bile acid 3α-sulfates can be determined.

EXAMPLE 3

Reagent (1): 25.2 mg of β-NAD (Oriental Yeast), 7.6 mg of nitro-blue tetrazolium (Dojin Kagaku Kenkyusho), and 10 units of diaphorase (Sigma) were dissolved in 25 ml of 50 mM tris-hydrochloric acid buffer solution (pH 8.0) containing 0.3% NOIGEN ET-189 (nonionic surface active agent, made by Daiichi Kogyo Seiyaku).

Reagent (2): 0.4N hydrochloric acid

Measurement: A 1.25 ml quantity of Reagent (1) was added to each of aqueous solutions (0.35 ml each) of lithocholic acid 3α-sulfate, sodium salt (Sigma) having various concentrations, and maintained at 37° C. for 5 minutes. To this mixture were added 0.05 ml of β-hydroxysteroid dehydrogenase (Sigma) solution (10 units/ml) and 0.1 ml of bile acid sulfate sulfatase (2 units/ml) in the order mentioned and mixed together. The resulting mixture was maintained at 37° C. for 10 minutes to develop color. Then 1.25 ml of Reagent (2) was added to stop the reaction, and the absorbance at 560 nm was measured. Excellent results as shown in FIG. 6 were obtained.

EXAMPLE 4

The serum with addition of glycolithocholic acid 3α-sulfate (GLCA-S) was diluted with additive-free serum to various concentrations, thereby giving test sera.

To 0.2 ml of the test serum were added 0.15 ml of distilled water and 1.25 ml of Reagent (1) used in Example 3, and the GLCA-S was determined in the same manner as in Example 3. The results are shown in Table 3.

TABLE 3

| GLCA-S concentration (μmol/liter) | Absorbance |
|---|---|
| 50 | 0.045 |
| 100 | 0.090 |
| 150 | 0.137 |
| 200 | 0.182 |

EXAMPLE 5

The serum with addition of GLCA-S and glycolithocholic acid (GLCA) was diluted to various concentrations with additive-free serum, thereby giving test sera.

To 0.2 ml of test serum were added 0.15 ml of distilled water and 1.25 ml of Reagent (1) of Example 3. Then the GLCA-S and GLCA were determined in the same manner as in Example 3 except that a mixture of β-hydroxysteroid dehydrogenase and 3β-hydroxysteroid dehydrogenase (Sigma) (10 units/ml each) was used in place of β-hydroxysteroid dehydrogenase solution The results are shown in Table 4.

TABLE 4

| GLCA-S concentration (μmol/liter) | GLCA concentration (←) | Absorbance |
|---|---|---|
| 25 | 25 | 0.044 |
| 50 | 50 | 0.091 |
| 75 | 75 | 0.135 |
| 100 | 100 | 0.180 |

Figure 1:
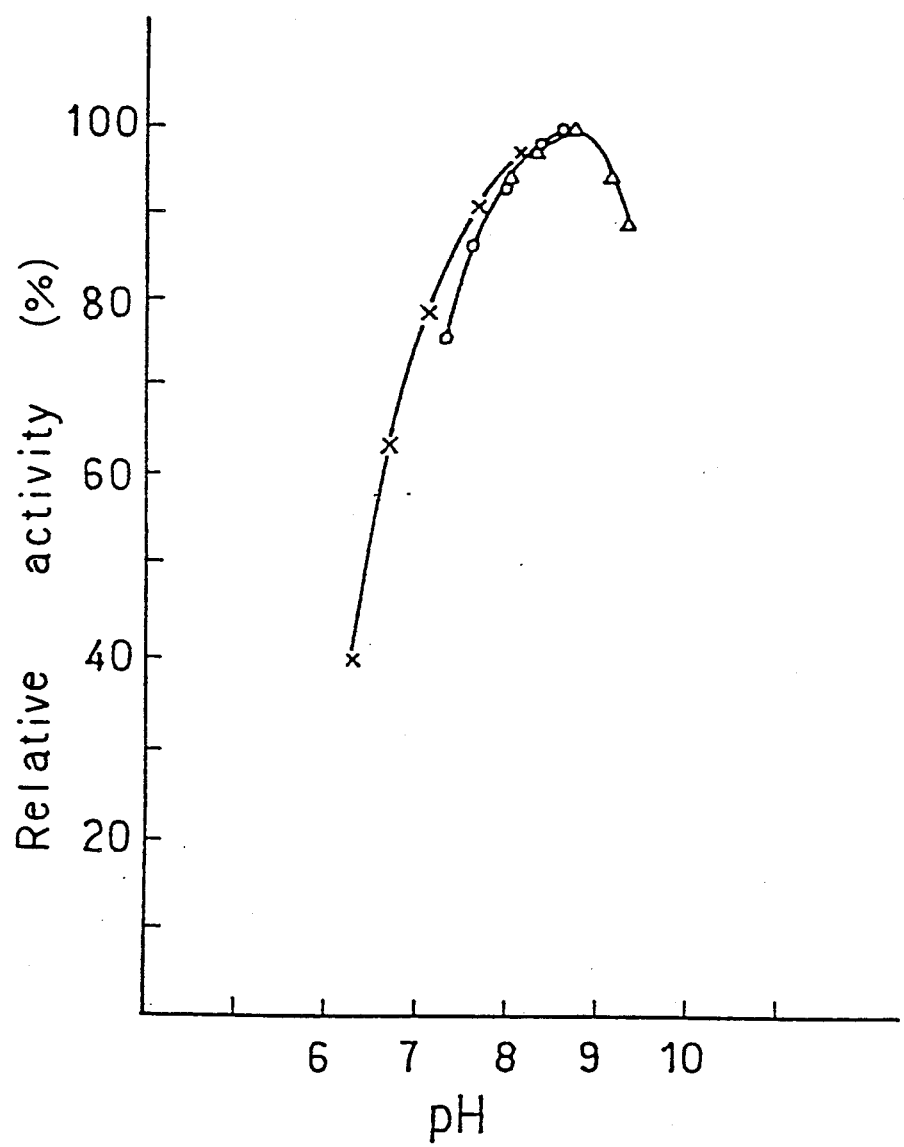
FIG. 1 is a graph showing the optimum pH of the present Enzyme.
Figure 2:
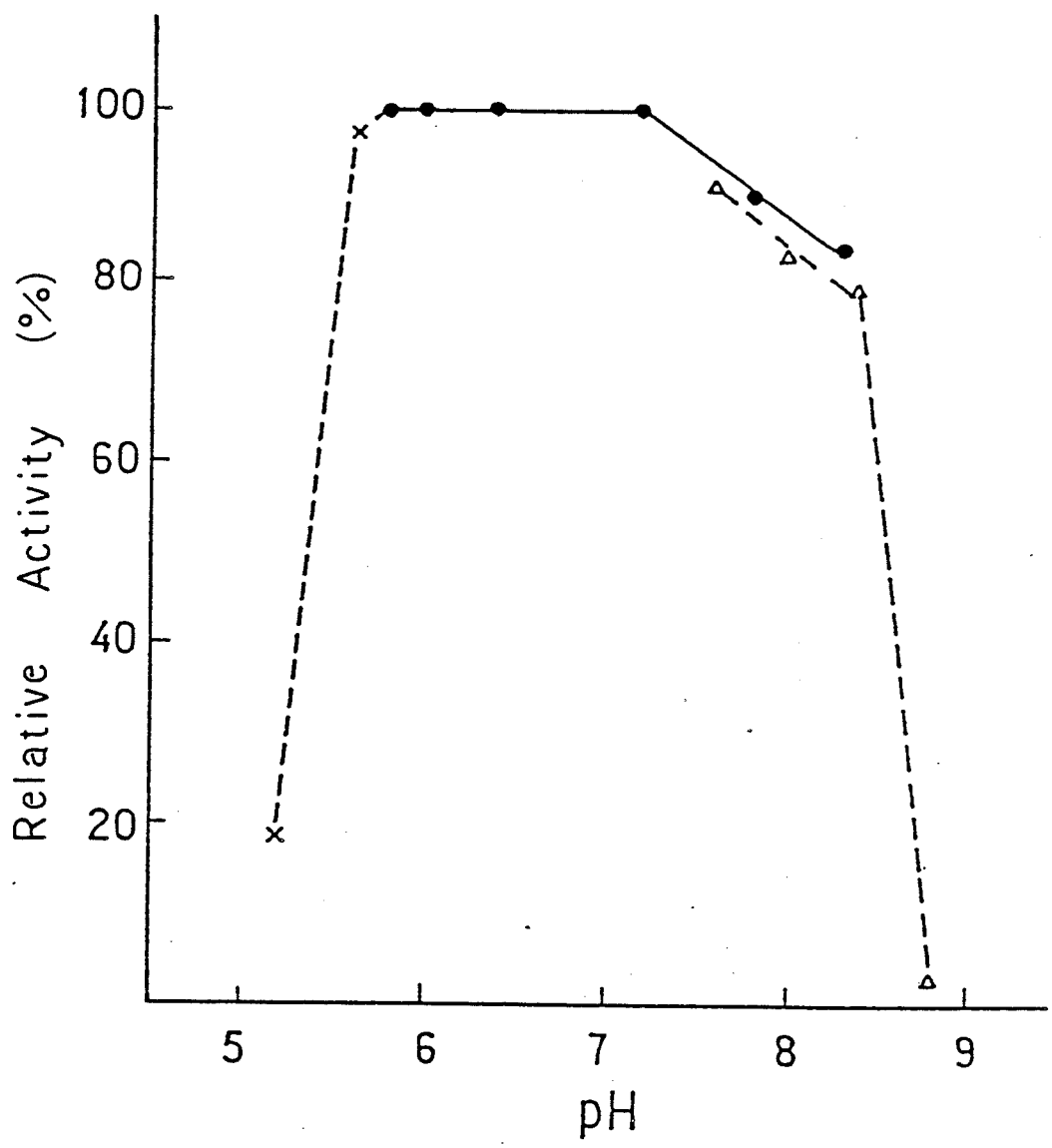
FIG. 2 is a graph showing the pH stability of the present Enzyme.
Figure 3:
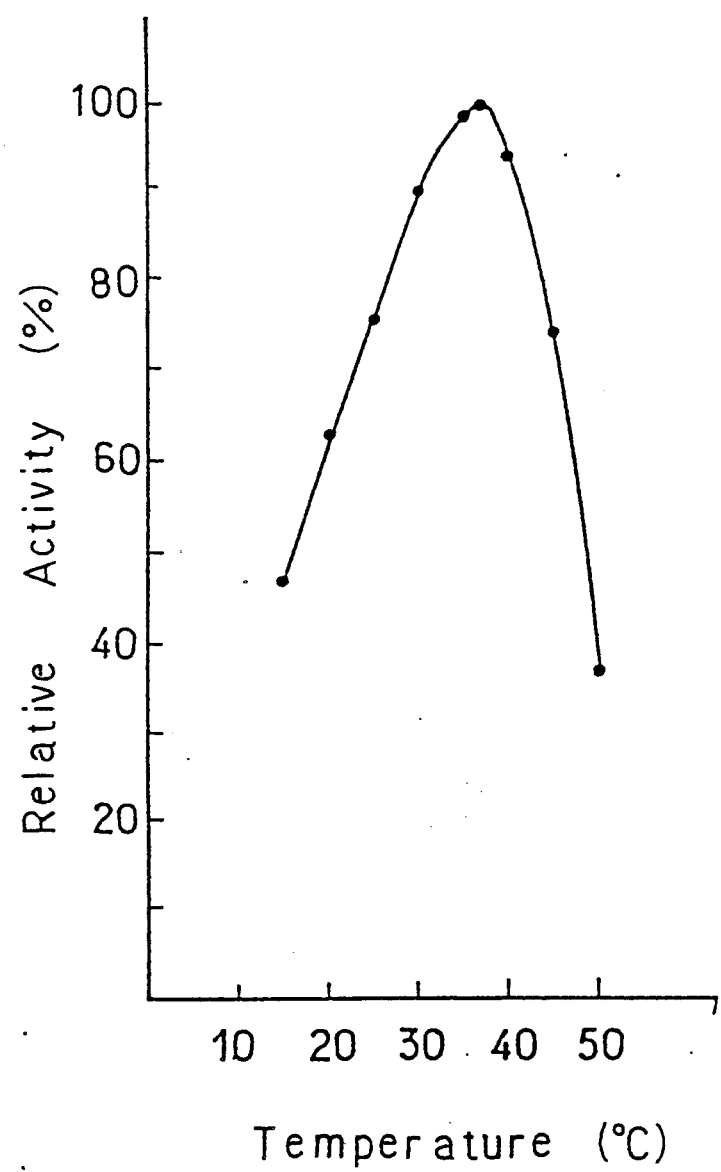
FIG. 3 is a graph showing the optimum temperature of the present Enzyme.
Figure 4:
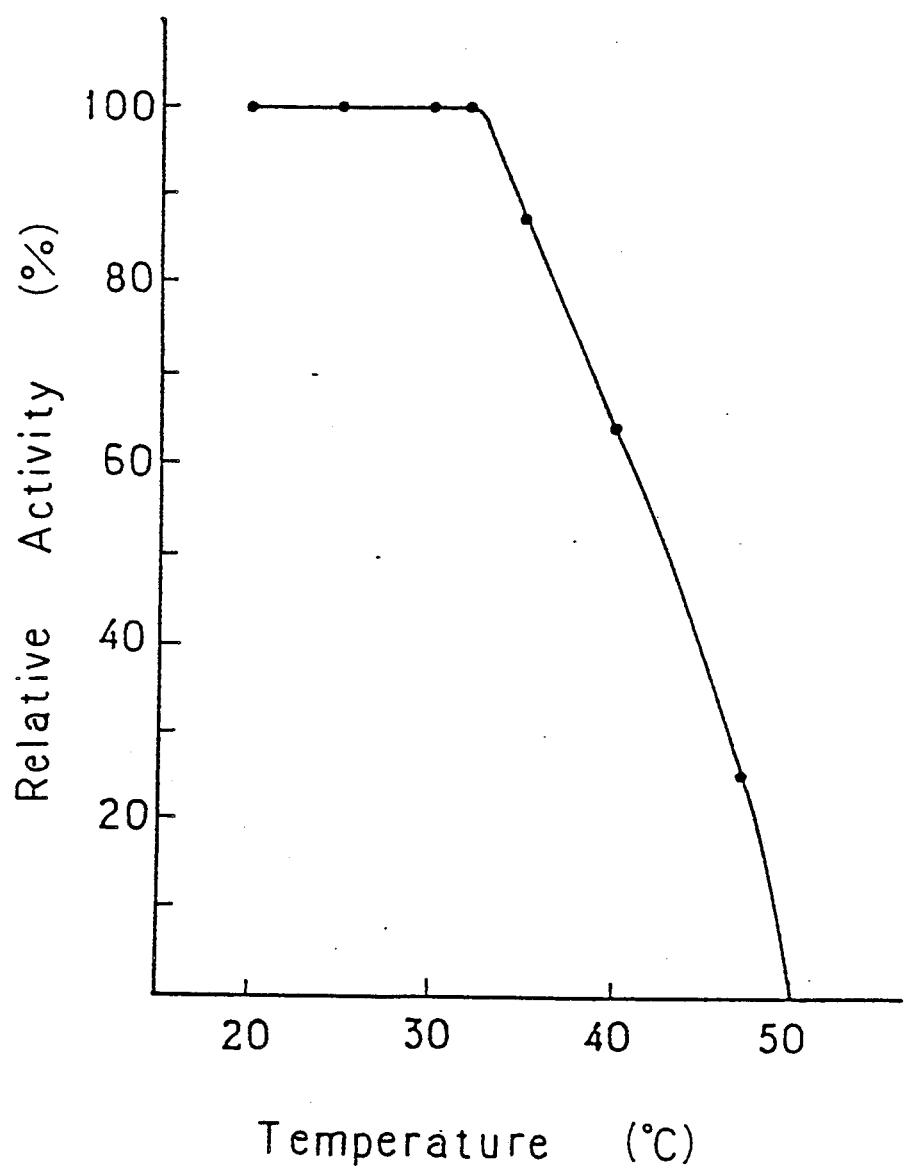
FIG. 4 is a graph showing the thermal stability of the present Enzyme.
Figure 5:
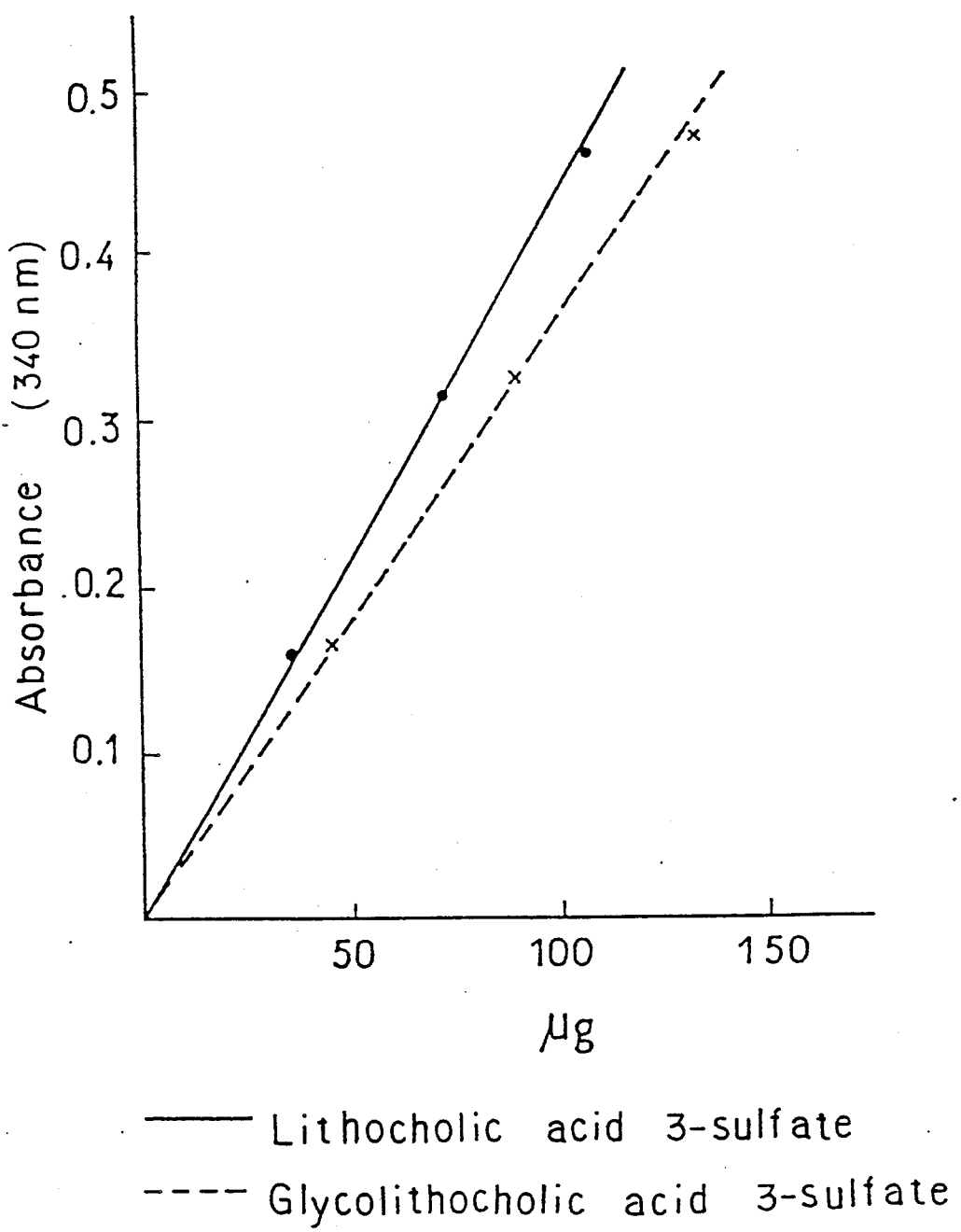
FIG. 5 and FIG. 6 are graphs showing the relation between the concentration of the substrate (bile acid 3α-sulfate) and absorbance obtained by practicing the method of the invention.
Figure 6:
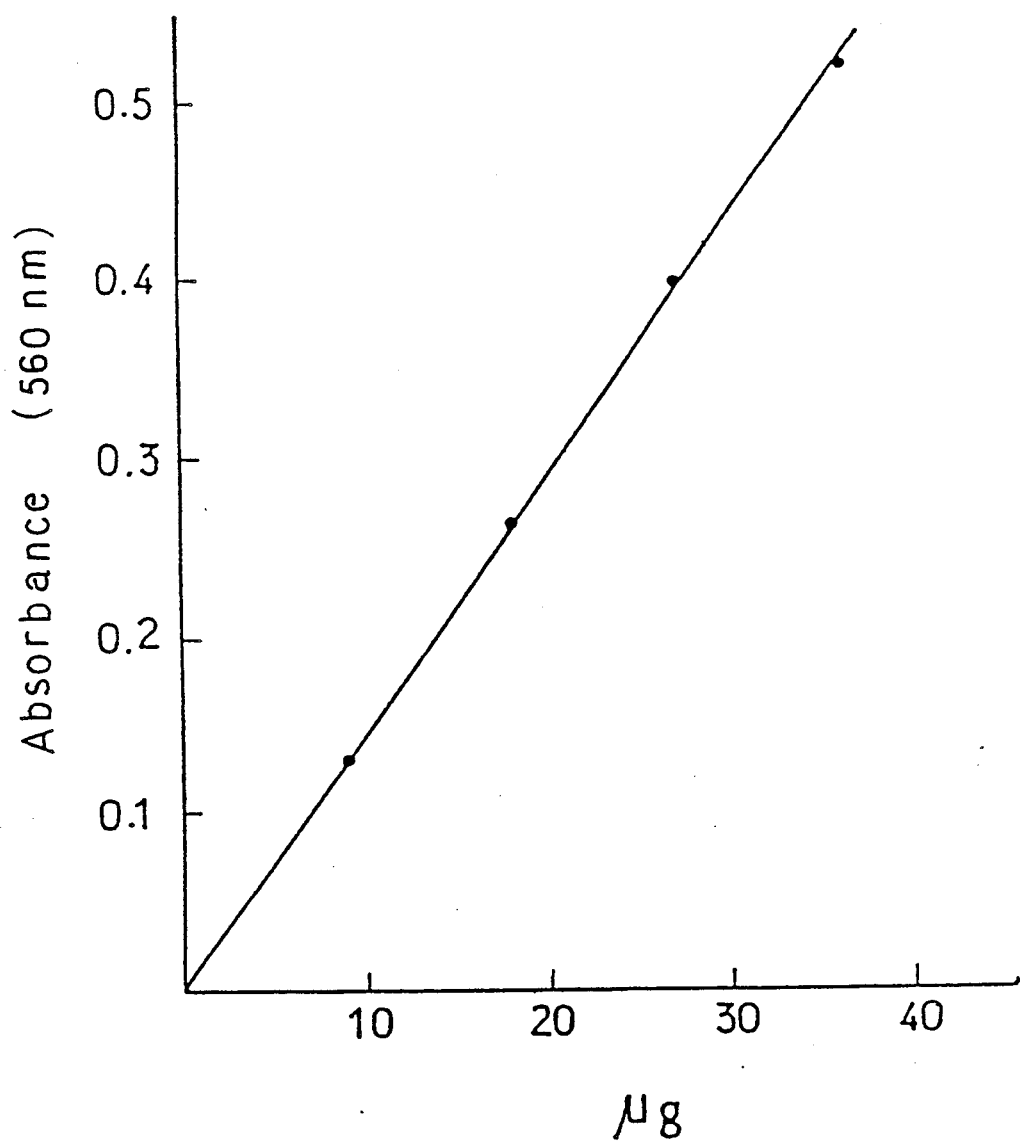

We claim:

1. A biologically pure form of a bile acid sulfate sulfatase having the following properties:
   (a) action: acting on 3α-sulfates of 5β-bile acids to hydrolyze the sulfate ester moiety thereof and to change the bonding configuration of the resulting OH group from α-configuration to β-configuration, thereby producting 3β-hydroxy bile acids;
   (b) substrate specificity: acting on 3α-sulfates of nonconjugated bile acids, and on 3α-sulfates each of gylcine-conjugated and taurine-conjugated bile acids;
   (c) optimum pH range: pH 8.5±0.5;
   (d) optimum temperature range: 35°±5° C.; and
   (e) molecular weight as determined by high performance liquid chromatography using gel filtration column: about 100,000.

* * * * *